(12) United States Patent
Allison-Rogers

(10) Patent No.: US 8,002,762 B2
(45) Date of Patent: Aug. 23, 2011

(54) POUCH FOR ABSORBENT PADS

(76) Inventor: Susan M. Allison-Rogers, Sandy Bay (AU)

( * ) Notice: Subject to any disclaimer, the term of this patent is extended or adjusted under 35 U.S.C. 154(b) by 0 days.

(21) Appl. No.: 10/592,126

(22) PCT Filed: Mar. 2, 2005

(86) PCT No.: PCT/AU2005/000298
§ 371 (c)(1),
(2), (4) Date: May 25, 2007

(87) PCT Pub. No.: WO2005/084601
PCT Pub. Date: Sep. 15, 2005

(65) Prior Publication Data
US 2008/0021433 A1  Jan. 24, 2008

(30) Foreign Application Priority Data

Mar. 5, 2004  (AU) ................................ 2004901183

(51) Int. Cl.
*A61F 13/15* (2006.01)
*A61F 13/20* (2006.01)
(52) U.S. Cl. ........ 604/397; 604/398; 604/399; 604/386; 604/387; 604/392; 604/393
(58) Field of Classification Search .................. 604/397, 604/398, 399, 400, 385.04
See application file for complete search history.

(56) References Cited

U.S. PATENT DOCUMENTS

| 780,598 | A | * | 1/1905 | Coleman et al. | 604/400 |
|---|---|---|---|---|---|
| 1,507,180 | A | * | 9/1924 | Wells | 604/397 |
| 1,695,153 | A | * | 12/1928 | Nelson | 604/397 |
| 2,571,357 | A | * | 10/1951 | Gemora | 604/397 |
| 2,840,078 | A | * | 6/1958 | Smith | 604/397 |
| 3,117,577 | A | * | 1/1964 | Mosier | 604/399 |
| 3,225,765 | A | * | 12/1965 | Mosier et al. | 604/397 |
| 4,759,754 | A | * | 7/1988 | Korpman | 604/387 |
| 5,019,064 | A | * | 5/1991 | Eilender | 604/378 |
| 5,137,526 | A | | 8/1992 | Coates | |
| 5,409,476 | A | | 4/1995 | Coates | |
| 5,422,387 | A | * | 6/1995 | Toms et al. | 524/52 |
| 5,722,127 | A | | 3/1998 | Coates | |
| 5,725,518 | A | | 3/1998 | Coates | |
| 5,752,946 | A | * | 5/1998 | Boberg et al. | 604/385.24 |
| 5,759,569 | A | * | 6/1998 | Hird et al. | 424/443 |
| 5,891,122 | A | | 4/1999 | Coates | |
| 6,231,970 | B1 | * | 5/2001 | Andersen et al. | 428/332 |

(Continued)

FOREIGN PATENT DOCUMENTS

AU  714528  1/2000

(Continued)

*Primary Examiner* — Leslie R Deak
*Assistant Examiner* — Susan Su
(74) *Attorney, Agent, or Firm* — Klarquist Sparkman, LLP

(57) ABSTRACT

A pouch for an absorbent pad is disclosed. The pouch (3) comprises a sheet of waterproof fabric formed into a pouch shape with a base (5) and a side wall (7) that extends from the base and is inwardly turned and defines an opening to insert a pad into the pouch so that the pouch covers the back and sides of the pad. In use, an assembly of the pouch and the pad received in the pouch can be positioned in a crotch region of an adult, child or baby in an operative position of the pad and with the pouch and the skin of the person enclosing the pad and forming a barrier to leakage from the pad.

16 Claims, 4 Drawing Sheets

U.S. PATENT DOCUMENTS

| | | |
|---|---|---|
| 6,254,583 B1 | 7/2001 | Coates |
| 6,419,666 B1* | 7/2002 | Mishima .................. 604/385.14 |
| 6,623,466 B1 | 9/2003 | Richardson |
| 6,895,603 B2 | 5/2005 | Coates |
| 6,926,705 B1 | 8/2005 | Coates |
| 2002/0028857 A1* | 3/2002 | Holy .............................. 523/124 |
| 2003/0145352 A1* | 7/2003 | Frohberg ...................... 800/284 |
| 2004/0158225 A1 | 8/2004 | Coates |
| 2004/0210206 A1 | 10/2004 | Coates |
| 2004/0236298 A1* | 11/2004 | Coates ..................... 604/385.04 |
| 2005/0210560 A1 | 9/2005 | Coates |
| 2009/0054548 A1* | 2/2009 | Wang et al. ................... 523/111 |
| 2009/0324917 A1* | 12/2009 | Wang et al. ................... 428/220 |

FOREIGN PATENT DOCUMENTS

| | | |
|---|---|---|
| CA | 2255465 | 4/2000 |
| WO | WO 93/23000 | 11/1993 |
| WO | WO 94/03137 | 2/1994 |
| WO | WO 02/067833 | 9/2002 |

* cited by examiner

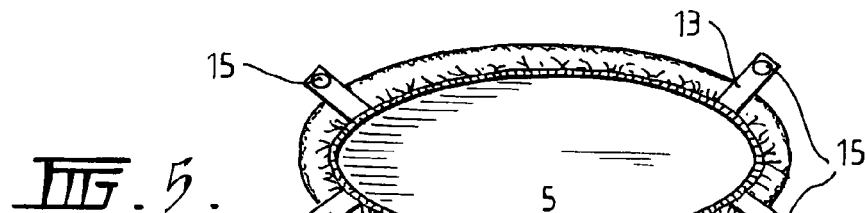
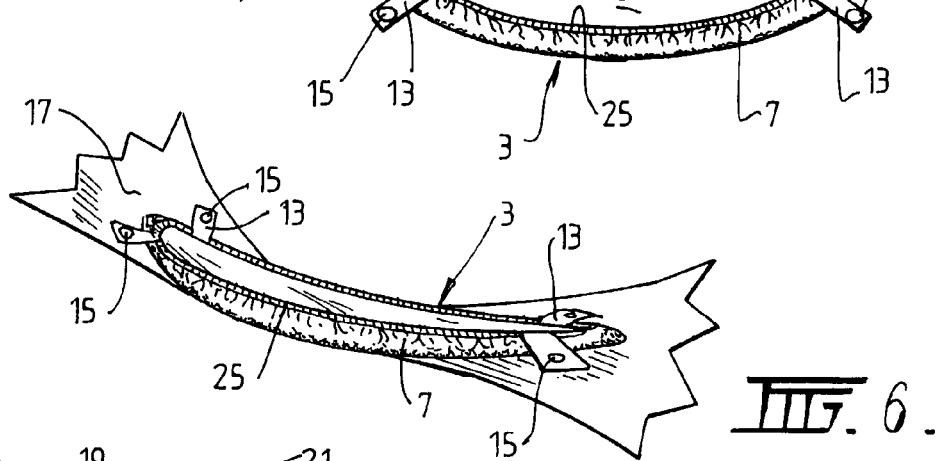
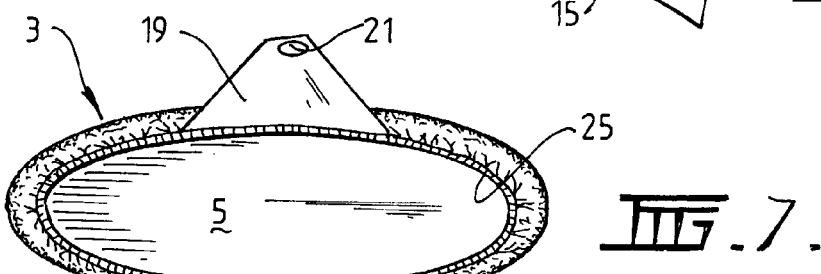
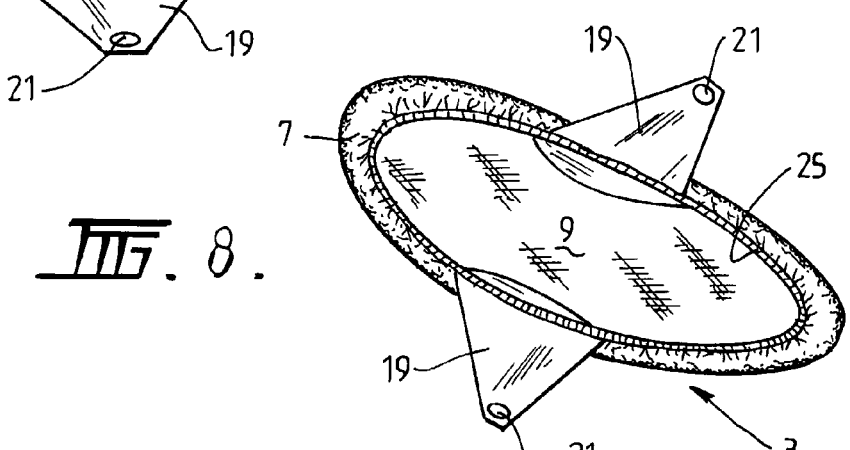
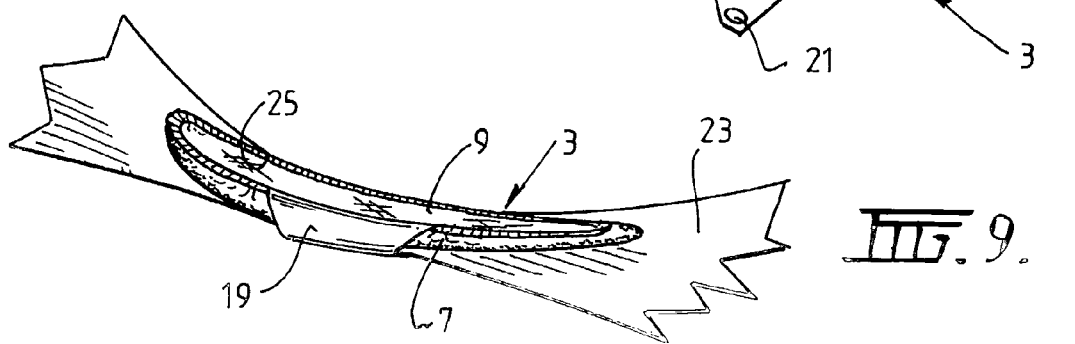

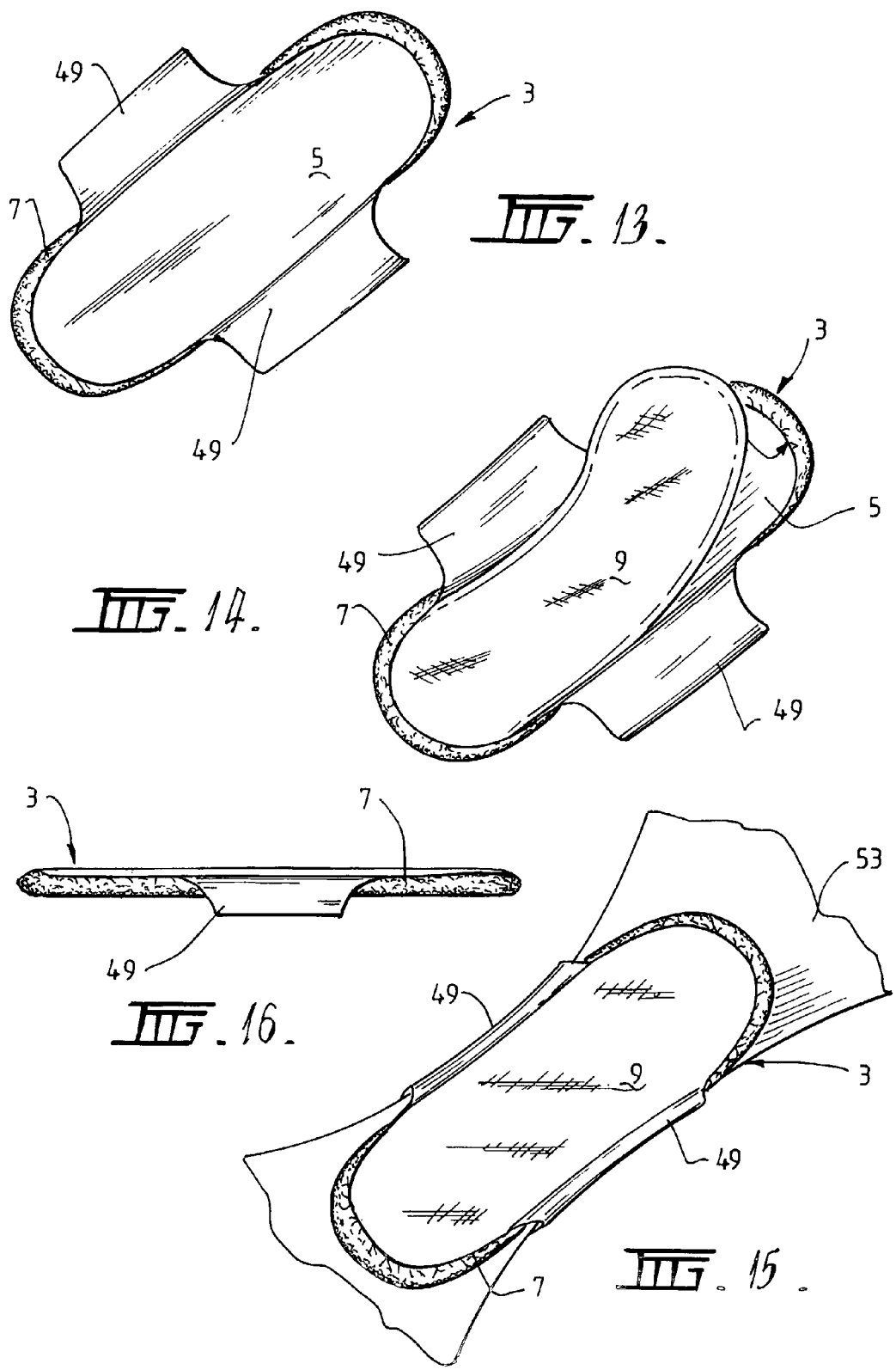

POUCH FOR ABSORBENT PADS

CROSS REFERENCE TO RELATED APPLICATIONS

This is the U.S. national stage of PCT Application No. PCT/AU2005/000298, filed Mar. 2, 2005, which claims the benefit of Australian Provisional Application No. 2004901183, filed Mar. 5, 2004, each of which applications is incorporated herein in its entirety by reference.

The present invention relates to a pouch for absorbent pads.

The term "absorbent pads" is understood herein to include absorbent pads that can be used by babies, women during menstruation, and adults and children during periods of incontinence.

The term "absorbent pads" includes pads that are compostable and flushable.

The term "absorbent pads" also includes pads that are non-compostable and non-flushable.

The term "absorbent pads" also includes pads that are reusable. In this context the term "pad" is understood herein to include cloth nappies.

The applicant is aware of a number of products in the patent literature that are designed to operably house absorbent pads to facilitate use of the pads by adults, children and babies. U.S. Pat. Nos. 4,664,663 and 6,764,477 are two examples of patents that relate to such products. The products known to the applicant tend to be relatively complex constructions that are made from a number of different components that are assembled together, typically by being glued together.

The present invention is another such product for housing absorbent pads.

In general terms, the product of the present invention is in the form of a pouch that is formed from a single waterproof member and thereby provides a high level of security against leakage for adults, children and babies using adsorbent pads and simplifies handling of the pads during and after pad changeover.

In addition, the pouch of the present invention makes it possible for the "absorbent pads" to be very simple and without the need for built-in waterproof backing, elastic or fasteners (as used in traditional one piece disposable nappies, sanitary pads and incontinence pads or garments). This in turn makes it possible for the "absorbent pads" to be simply constructed from materials which allow it to be both flushable and or compostable, and thus enabling the disposable part of the system to be easily and economically 'recycled'. The resultant product is a two part system which is more ecologically friendly.

According to the present invention there is provided a pouch for an absorbent pad, the pad having a back, front and sides, the pouch comprising a waterproof member formed into a pouch shape with a base and a side wall that extends from the base and is inwardly turned and defines an opening to insert a pad into the pouch so that the pouch covers the back and sides of the pad whereby, in use, an assembly of the pouch and the pad received in the pouch can be positioned in a crotch region of an adult, child or baby in an operative position of the pad and with the pouch and the skin of the person enclosing the pad and forming a barrier to leakage from the pad.

The use of a single waterproof member to form the pouch avoids the disadvantage of known products that require the use of adhesives or other fastening options to assemble together separate components that form the products. The use of a single waterproof member also facilitates forming the member into the pouch shape. A pouch shape is advantageous because, as the term "pouch" is used herein, a pouch has a structure that defines a discrete space into which a pad can be inserted. The construction of many of the known products is such that significantly more effort is required to open up the product to allow placement of a pad into the product.

The pouch may be re-usable.

Preferably the pouch comprises a base that has the same general shape as the pad.

The side wall may be elasticised to pull the side wall inwardly thereby to form the above pouch shape.

By way of further example, the pouch may be formed by heat-forming the waterproof member thereby to form the above pouch shape.

The heat forming process may comprise heating a sheet of the waterproof member and positioning the heated sheet into a die that defines the pouch shape and applying a vacuum to force the heated sheet against the die wall.

Preferably the side wall of the pouch is formed so that the pouch has a curved shape along its length and is thereby more adapted by virtue of the curved shape to be positioned in the crotch region of the adult, child, or baby.

Preferably the side wall of the pouch defines an opening that is smaller than the surface area of the front of the pad so that, in use, the pad has to be manipulated to be positioned in the pouch.

Preferably a free edge of the side wall of the pouch that contacts the skin of the adult, child, or baby in use of the pouch is formed from a "soft" material to maximise comfort for the adult, child, or baby.

Preferably a free edge of the side wall of the pouch that contacts the skin of the adult, child, or baby in use of the pouch comprises a rounded bead of soft material to maximise comfort for the adult, child, or baby.

The pouch may comprise a means for releasably holding or attaching the pouch to an item of clothing, which may be by way of example an item of underwear in the case of adults and children or outer "pants" in the case of babies.

Preferably the attachment means comprises press-studs or other suitable connection means on the pouch and the item of clothing.

In one particular embodiment it is preferred that the attachment means comprises:
 (a) a pair of flaps extending from opposite sides of the pouch that can be folded around an item of underwear so that the ends of the flaps overlap to a certain extent; and
 (b) press-studs or other suitable connection means that can connect the folded flaps together.

The pouch may comprise a means for tying or otherwise fastening the pouch around a wearer.

According to the present invention there is also provided an assembly of the above-described pouch and an absorbent pad fitted in the pouch.

The present invention is described further by way of example with reference to the accompanying drawings, of which:

FIG. 5 is a top plan view of another embodiment of a pouch in accordance with the present invention;

FIG. 6 is a perspective view of the pouch shown in FIG. 5 secured to an undergarment;

FIG. 7 is a top plan view of another, although not the only other possible, embodiment of a pouch in accordance with the present invention;

FIG. 8 is a top plan view illustrating an assembly of the pouch shown in FIG. 7 and an absorbent pad located within the pouch;

FIG. 9 is a perspective view illustrating the assembly of the pouch and absorbent pad shown in FIG. 8 secured to an undergarment;

FIG. 13 is a top plan view of another, although not the only other possible, embodiment of a pouch in accordance with the present invention;

FIG. 14 is a perspective view that illustrates one method of fitting an absorbent pad into the pouch shown in FIG. 13;

FIG. 15 is a perspective view illustrating the assembly of the pouch and absorbent pad shown in FIG. 14 secured to an undergarment; and FIG. 16 is a side view of the assembly shown in FIG. 15.

Figure 1:
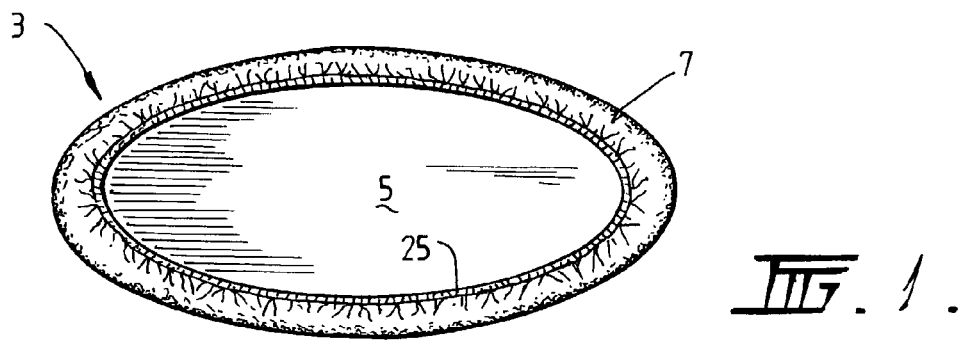
FIG. 1 is a top plan view of one embodiment of a pouch in accordance with the present invention.

The embodiment of the pouch 3 shown in FIGS. 1 to 4 is formed from a single sheet of a waterproof material so that it comprises a base 5 and a side wall 7 that extends upwardly and inwardly from the base 5.

The pouch 3 is adapted to snuggly receive an absorbent pad 9, with the back and sides of the pad being located in the pouch 3 and the front 11 of the pad facing outwardly.

The pouch 3 is generally oval-shaped and curved along the length of the pouch. The oval shape is selected to match the general shape of the pad 9.

The sheet of waterproof fabric that forms the pouch 3 is elasticised around the perimeter thereof. Elasticising the sheet gathers the flat sheet into the pouch shape, ie with the upwardly and inwardly formed side wall 7.

The elasticised construction is such that the pouch 3 can be readily washed so that the pouch can be reused.

Figure 4:
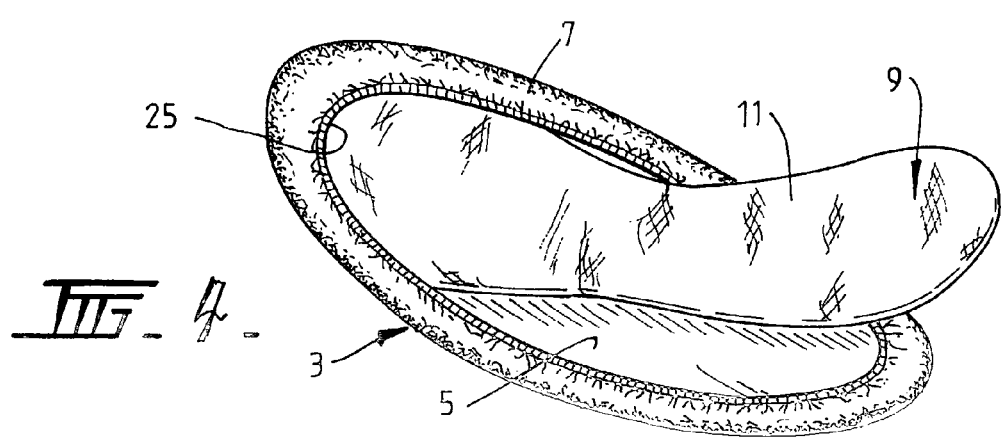
FIG. 4 is a perspective view that illustrates one method of fitting the absorbent pad into the pouch to form the assembly shown in FIG. 3.

FIG. 4 illustrates one method of fitting the pad 9 into the pouch 3. The method comprises sliding one end of the pad 9 into one end of the pouch 3 and thereafter manipulating the remainder of the pad into the pouch, working from the fitted end to the opposite end.

Figure 2:
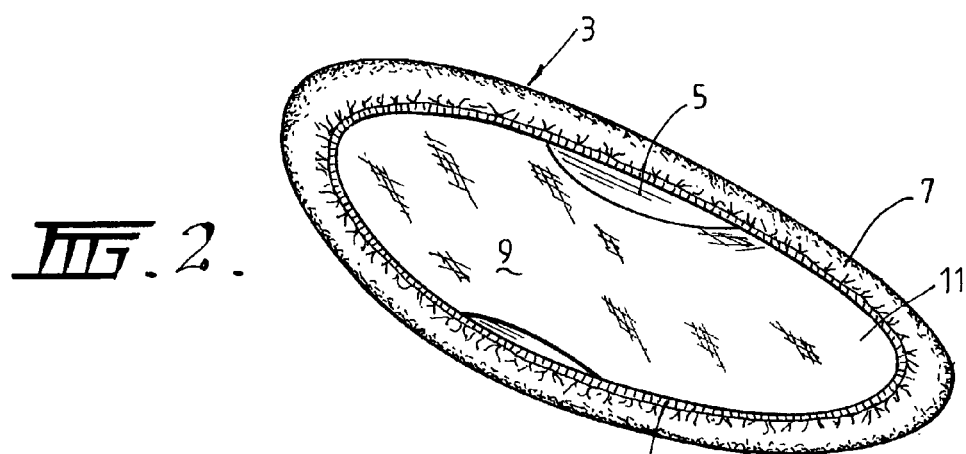
FIG. 2 is a top plan view of an assembly of the pouch shown in FIG. 1 and an absorbent pad located in the pouch.
Figure 3:
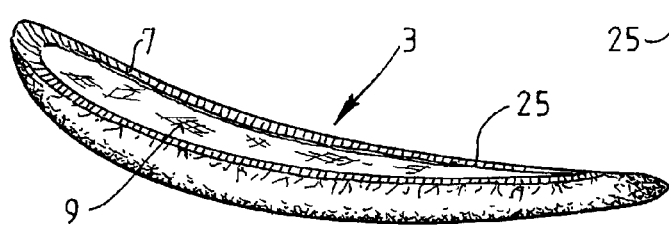
FIG. 3 is a perspective view of the assembly of the pouch and the pad shown in FIG. 2.

It can readily be appreciated that the assembly of the pouch 3 and the pad 9 shown in FIGS. 2 and 3 is suitable to be positioned in the crotch region of a adult, child or baby and held in position by an item of clothing.

In the case of adults and children the item of clothing may be, by way of example, underwear. In the case of babies the item of clothing may be, by way of example, an outer pair of baby "pants".

It can also be appreciated that when the assembly is properly positioned, with the pad in an operative position, the upwardly and inwardly directed side wall 7 contacts the skin of the person, with the result that the fitted pad 9 is enclosed and there is minimal risk of leakage from the pad 9.

The free edge of the side wall 7 comprises a rounded bead 25 of soft material. The bead-shape and the material selection maximise comfort for a person wearing the assembly of the pouch 3 and the pad 9.

The location of the assembly in an optimum position may be facilitated by the use of adhesive.

The embodiments of the pouch 3 shown in FIGS. 5 to 11 have the same basic construction as the pouch 3 shown in FIGS. 1 to 4 in that the pouches 3 are also formed by elasticising sheets of waterproof fabric and thereby gathering the sheets into the pouch shapes shown in the figures.

The pouches 3 shown in FIGS. 5 to 9 further comprise means to releasably attach or hold the assemblies of the pouches 3 and the pads 9 to items of clothing.

The attachment means shown in FIGS. 5 and 6 comprises a series of straps 13 that extend from the side wall 7 at the ends of the pouch 3, male or female parts of press studs 15 connected to the straps 13, and complementary male or female parts of press studs on an inside surface of an item of underwear 17 (shown in FIG. 6 only).

In use, the assembly of the pouch 3 and the pad 9 shown in FIG. 6 can be conveniently connected to and thereafter released from the underwear 17 by means of the press studs 15.

The attachment means shown in FIGS. 7 to 9 comprises a pair of flaps or wings 19 extending from the side wall 7 on opposite sides of the pouch 3, a male or female part of a press studs 21 connected to one of the flaps 19, and a complementary male or female part of the press stud 21 connected to the other flap 19.

In use, the flaps 19 can be folded rearwardly around the outwardly facing surface of an item of underwear 23 into an overlapping relationship and thereafter the male and female parts of the press stud 21 can be pressed together to secure the pouch 3 around the crutch of the underwear 23 (shown in FIG. 9 only).

Figure 10:
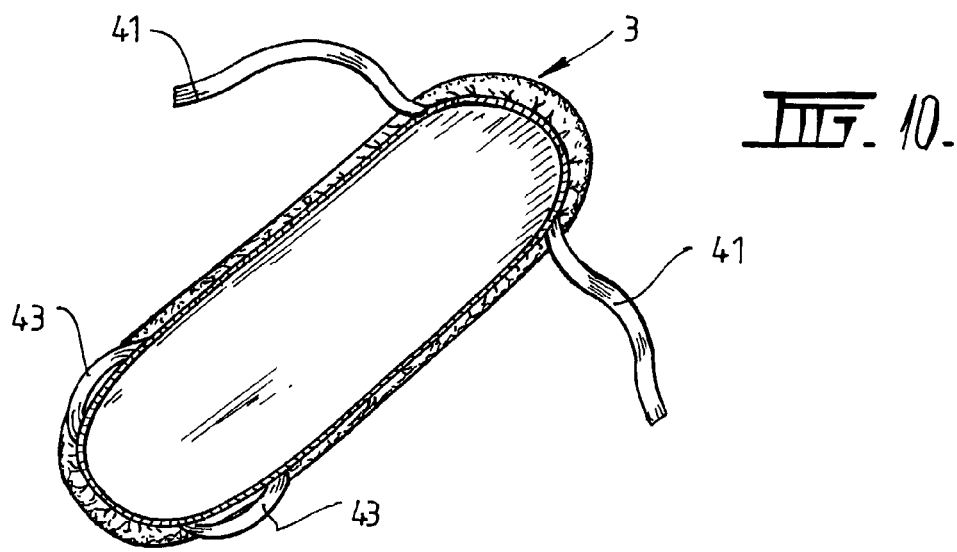
FIG. 10 is a top plan view of another, although not the only other possible, embodiment of a pouch in accordance with the present invention.
Figure 11:
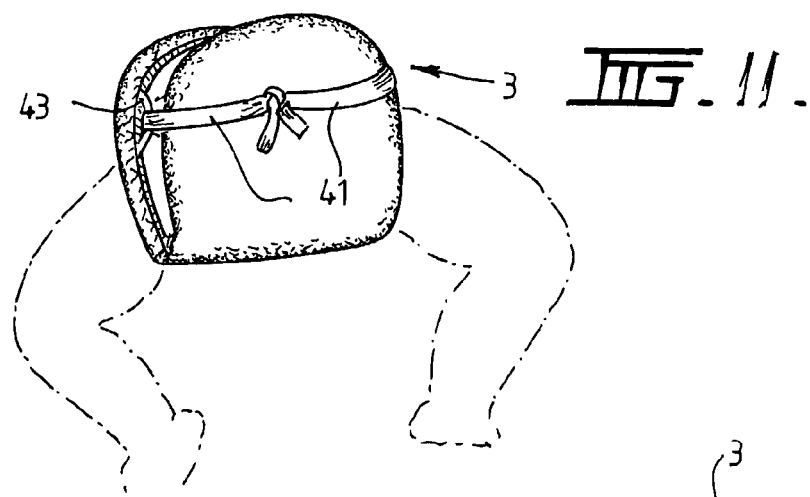
FIG. 11 is a schematic perspective view illustrating how the pouch shown in FIG. 10 can be tied to a baby.

The FIG. 10 pouch has a more rectangular shape than the FIGS. 1 to 9 pouches 3 and includes a pair of ties 41 at one end and a pair of looped openings 43 at the other end that facilitate securing an assembly of the pouch 3 and a pad (not shown) inserted into the pouch to a wearer, such as baby—as shown in FIG. 11—rather than to an item of clothing.

Figure 12:
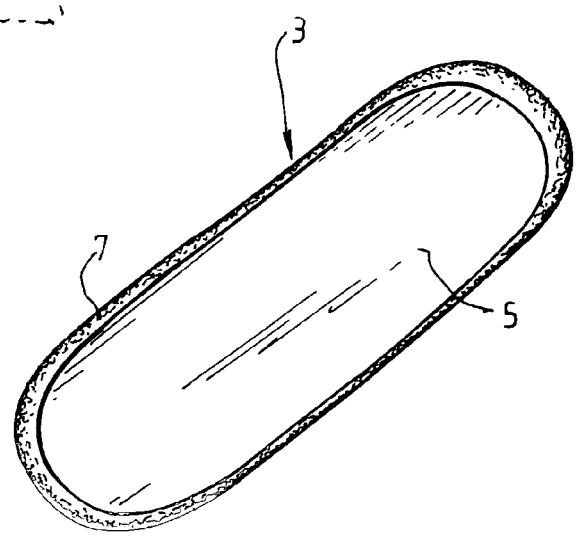
FIG. 12 is a top plan view of another, although not the only other possible, embodiment of a pouch in accordance with the present invention.

The pouch 3 shown in FIG. 12 is similar to the pouches shown in FIGS. 1 to 11.

The FIG. 12 pouch has a similar rectangular shape to the FIGS. 10/11 pouch 3.

However, the FIG. 12 pouch 3 has two particular features that are not in the FIGS. 1 to 11 pouches.

Firstly, the FIG. 12 pouch is a generally flat construction and does not have a curved shape along the length of the pouch 3.

Secondly, the FIG. 12 pouch is formed into the pouch shape shown in the figure by heat-forming a single sheet of waterproof material in a die rather than by securing elastic around the perimeter of a sheet of waterproof material, as described in relation to the FIGS. 1 to 11 pouches. The heat formed pouch is more likely to be semi-reusable, for example used for a day with some pad changes and then disposed of as a waste product. In this application, preferably the pouch is made from a biodegradable plastic material, such as a starch-based plastic material. Moreover, in this application, typically an assembly of the pouch and a pad, in use, is held in place by means of adhesive securing the assembly to an item of underwear.

The embodiment of the pouch 3 shown in FIGS. 13 to 16 is the same basic construction as the pouch 3 shown in FIG. 12.

The pouches 3 shown in FIGS. 13 to 16 further comprises a means to releasably attach or hold the assembly of the pouch 3 and the pad 9 to an item of clothing.

As described in relation to the FIGS. 5 to 9 pouches, in the case of adults and children the item of clothing may be, by way of example, underwear. In the case of babies the outer piece of clothing may be by way of example an outer pair of baby "pants".

The attachment means shown in FIGS. 13 to 16 comprises a pair of flaps or wings 49 extending from the side wall 7 on opposite sides of the pouch 3 and having Velcro, adhesive or other means to facilitate securing the wings to an item of underwear 53.

In use, the wings 19 can be folded rearwardly around the item of underwear 53 and thereafter secured to the undergarment 23.

The same method described above to fit absorbent pads 9 into the FIGS. 1 to 4 pouch may be used to fit absorbent pads 9 into the FIGS. 12 to 15 pouches 3. With reference to FIG. 14, the method comprises sliding one end of the pad 9 into one end of the pouch 3 and thereafter manipulating the remainder of the pad into the pouch, working from the fitted end to the opposite end.

The above-described pouches 3 provide a greater level of security against leakage for adults, children and babies using absorbent pads 9 and simplify handling of the pads during and after pad changeover.

A significant advantage of the above-described pouches 3 is that they make it possible to greatly simplify the construction of the absorbent pads 9. This is a clear and significant difference from many current pads that include built in waterproof backing, elastic, or fasteners that complicate the construction and cost of the pads and make it difficult and expensive to dispose of the pads in an environmentally sensitive way. The above-described pouches 3 make it possible to construct the pads solely for the absorption of fluids and consequently the pads can be designed to be bio-degradable in a practical way.

Many modifications may be made to the embodiments of the pouch of the present invention described above without departing from the spirit and scope of the invention.

By way of example, whilst the embodiments of the pouch of the present invention are formed into the pouch shapes shown in the figures by elasticising and heat forming the pouches, the present invention is not so limited and extends to any suitable constructions of pouch-shape.

The invention claimed is:

1. A diaper system comprising a pouch and an absorbent biodegradable pad, the pad having a back, front and sides, the pouch comprising a single oval waterproof member formed into a pouch shape with a base and a side wall that extends from the base and is inwardly turned and defines an oval opening to insert a pad into the pouch so that the pouch covers the back and sides of the pad whereby, in use, an assembly of the pouch and the pad received in the pouch can be positioned in a crotch region of an adult, child or baby in an operative position of the pad and with the pouch configured to contact the skin of the person so as to enclose the pad and forming a barrier to leakage from the pad;

wherein the side wall has a seamless curved shape extending continuously around its length and width and a continuously curved oval edge that is elasticized and gathered around the perimeter of the side wall to pull the side wall inwardly to form the pouch and maintain its shape, wherein the single waterproof member and pad form the only fluid containment and absorption layers;

the pouch including straps connected to corners of the elasticized edge to facilitate releasable attachment of the pouch to an item of clothing.

2. The pouch defined in claim 1 further comprising a base that has the same general shape as the pad, the base having a substantially oval shape.

3. The pouch of claim 1 wherein the waterproof member is made from a biodegradable starch-based plastic material.

4. The pouch defined in claim 3 wherein the side wall of the pouch is formed so that the pouch has a curved shape along its length and is thereby more adapted by virtue of the curved shape to be positioned in the crotch region of the adult, child, or baby.

5. The pouch defined in claim 1 wherein the side wall of the pouch defines an opening that is smaller than the surface area of the front of the pad so that, in use, the pad has to be manipulated to be positioned in the pouch.

6. The pouch defined in claim 1 wherein a free edge of the side wall of the pouch that is configured to be in contact with the skin of the adult, child, or baby in use of the pouch is formed from a soft material to maximise comfort for the adult, child, or baby.

7. The pouch defined in claim 1 wherein a free edge of the side wall of the pouch that is configured to be in contact with the skin of the adult, child, or baby in use of the pouch comprises a rounded bead of soft material to maximise comfort for the adult, child, or baby.

8. The pouch defined in claim 1 further including press-studs secured to the straps.

9. A diaper system comprising a pouch and an absorbent compostable pad, the pad having a back, front and sides, the pouch comprising a single oval waterproof member formed into a pouch shape with a base and a side wall that extends from the base and is inwardly turned and defines an oval opening to insert the pad into the pouch so that the pouch covers the back and sides of the pad whereby, in use, an assembly of the pouch and the pad received in the pouch can be positioned in a crotch region of an adult, child or baby in an operative position of the pad and with the pouch configured to contact the skin of the person so as to enclose the pad and forming a barrier to leakage from the pad;

wherein the side wall has a seamless curved shape extending continuously around its length and width and a continuously curved oval edge that is elasticized and gathered around the perimeter of the side wall to pull the side wall inwardly to form the pouch and maintain its shape, wherein the single waterproof member and pad form the only fluid containment and absorption layers; and a pair of ties extending from corners of the elasticized edge and corresponding loops extending from opposite corners of the elasticized edge.

10. A diaper system comprising a pouch, item of clothing and an absorbent compostable pad, the pad having a back, front and sides, the pouch comprising a single waterproof member formed into a pouch shape with a base and a side wall that extends from the base and is inwardly turned and defines an opening to insert a pad into the pouch so that the pouch covers the back and sides of the pad, the side wall having a seamless curved shape extending continuously around its length and width and being elasticized and gathered around the perimeter of the side wall to pull the side wall inwardly thereby to form the above pouch shape and maintain its shape, and attachment members in the form of a series of straps that are connected to the elasticized perimeter of the side wall at the ends of the pouch without compromising the waterproofing of the pouch and press-studs connected to the straps for releasably attaching the pouch to the item of clothing, whereby, in use, an assembly of the pouch and the pad received in the pouch can be positioned in a crotch region of an adult, child or baby in an operative position of the pad such that the pouch forms a barrier to leakage from the pad, the straps being connected at least to four corners of the elasticized perimeter to allow the item of clothing when worn and connected to the straps to open up the pouch by stretching of the elasticized perimeter.

11. The pouch of claim 10 wherein the pouch is made of a biodegradable plastic material and is reusable and the pad is made of a flushable material.

12. A diaper system for use by incontinent users comprising:
- an absorbent flushable pad having a back, front and sides;
- a pouch having a base and a side wall that extends from the base and terminates at an edge that defines an opening into which the pad is inserted such that the pouch covers the back and sides of the pad, the edge of the pouch being elasticized and gathered to pull the side wall inwardly and upward to form the pouch and maintain the shape of the pouch, the base and side wall having a seamless surface that extends continuously around its length and width and encloses the back and sides of the pad, the pouch including a first set of separate fasteners located at least at four corner locations of the elasticized edge, the pouch being formed from a single piece of substantially waterproof material, the pad and single piece of waterproof material acting as the only fluid containment and absorbent layers; and
- an item of clothing having a second set of fasteners to which the first set of fasteners are attached, the pouch and item of clothing cooperating to secure the edge of the pouch against the user's body.

13. The diaper system of claim 12 wherein the pad is made of a compostable material and the pouch is reusable.

14. The diaper system of claim 12 wherein the first set of fasteners includes straps extending from the elasticized edge at the corner locations.

15. A diaper system for use by incontinent users comprising:
- an absorbent biodegradable pad;
- a single piece of waterproof material having a shape complementary to the pad and an elasticized, gathered edge that draws upwardly a sidewall of the material to form a pouch with an opening, the opening being sized smaller than the pad, the pad being securely retained within and yet removable from the pouch without being attached to the pouch, the elasticized, gathered edge forming a part of the waterproof material and cooperating with the waterproof material to maintain the material in a pouch shape while allowing the opening to be stretchably expanded;
- the pouch having a seamless surface that extends continuously around its length and width, and including a first set of fasteners located at least at four corner locations of the elasticized edge; and
- an outer garment having a second set of fasteners complementary to the first set of fasteners to releasably attach the elasticized edge of the pouch to the outer garment.

16. The diaper system of claim 15 wherein the pad is a flushable material.

* * * * *